(12) United States Patent  (10) Patent No.: US 7,949,408 B2
Bonde et al.  (45) Date of Patent: May 24, 2011

(54) SYSTEM AND METHOD FOR ELECTRICALLY PROBING AND PROVIDING MEDICAL ELECTRICAL STIMULATION

(75) Inventors: Eric H. Bonde, Minnetonka, MN (US); Eric M. Stetz, Lino Lakes, MN (US); Carole A. Tronnes, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 1346 days.

(21) Appl. No.: 11/413,310

(22) Filed: Apr. 28, 2006

(65) Prior Publication Data

US 2007/0255371 A1  Nov. 1, 2007

(51) Int. Cl.
*A61N 1/05* (2006.01)
(52) U.S. Cl. ............. 607/116; 607/115; 607/117; 607/2
(58) Field of Classification Search .................. 604/164, 604/22, 20, 158, 506, 264, 523; 607/116–117, 607/7, 15, 16; 606/12, 15, 16
See application file for complete search history.

(56) References Cited

U.S. PATENT DOCUMENTS

| | | | |
|---|---|---|---|
| 3,664,329 A | 5/1972 | Naylor | |
| 4,187,853 A | 2/1980 | Barton et al. | |
| 5,957,965 A | 9/1999 | Moumane et al. | |
| 6,055,456 A | 4/2000 | Gerber | |
| 6,104,960 A | 8/2000 | Duysens et al. | |
| 6,224,566 B1 * | 5/2001 | Loeb | 604/22 |
| 6,512,958 B1 | 1/2003 | Swoyer et al. | |
| 6,718,212 B2 | 4/2004 | Parry et al. | |
| 6,847,849 B2 | 1/2005 | Mamo et al. | |
| 6,971,393 B1 | 12/2005 | Mamo et al. | |
| 6,999,819 B2 | 2/2006 | Swoyer et al. | |
| 2001/0025192 A1 * | 9/2001 | Gerber et al. | 607/117 |
| 2003/0028232 A1 | 2/2003 | Camps et al. | |
| 2003/0045919 A1 | 3/2003 | Swoyer et al. | |
| 2006/0206162 A1 | 9/2006 | Wahlstrand et al. | |
| 2006/0206163 A1 | 9/2006 | Wahlstrand et al. | |
| 2006/0217655 A1 * | 9/2006 | Vitullo et al. | 604/21 |
| 2007/0050004 A1 | 3/2007 | Swoyer et al. | |

FOREIGN PATENT DOCUMENTS

| | | |
|---|---|---|
| WO | 9725099 | 7/1997 |
| WO | 02087678 | 11/2002 |
| WO | 2004012809 | 2/2004 |

OTHER PUBLICATIONS

K. Carlton et al., "Canine Evaluation of the InterStim® Tined Anchor: Acute Holding Strength," 4 pgs., 2002.
Medtronic Technical Manual entitled "InterStims®—Test Stimulation Lead Kit, For Use with Model 3625 Test Stimulator," 28 pgs., 2002.
Medtronic Instruction Manual entitled "InterStim®—Test Stimulation Components," 40 pgs., 2002.

* cited by examiner

*Primary Examiner* — Carl H Layno
*Assistant Examiner* — Paula J Stice

(57) ABSTRACT

A system for providing medical electrical stimulation including a lead assembly and a cannula. The lead assembly includes a lead body and a needle tip. The lead body has a distal section and a proximal section. The needle tip is formed of an electrically conductive material and is connected to the distal section of the lead body. The lead body is slidably disposed within a cannula lumen, with a distal end of the cannula being selectively connected to an abutment surface of the needle tip such that the needle tip extends distal the cannula to define a needle probe. With this construction, the lead assembly can be delivered to a desired implantation site via manipulation of the cannula and/or energization of the needle tip, and the cannula can be removed from the lead body without requiring movement of the needle tip.

23 Claims, 11 Drawing Sheets

SYSTEM AND METHOD FOR ELECTRICALLY PROBING AND PROVIDING MEDICAL ELECTRICAL STIMULATION

BACKGROUND OF THE INVENTION

The present invention relates to systems and methods for providing electrical stimulation to bodily tissue, such as a portion of a patient's nervous system. More particularly, it relates to temporarily implantable electrical leads, such as a peripheral nerve evaluation lead used to stimulate a sacral nerve, that facilitate probing and implantation, and in some embodiments are bipolar.

A number of human bodily functions are affected by the nervous system. For example, bodily disorders, such as urinary incontinence, urinary urge/frequency, urinary retention, pelvic pain, bowel dysfunction (constipation, diarrhea, etc.), erectile dysfunction, etc., are all bodily functions influenced by the sacral nerves. As a point of reference, urinary incontinence is the involuntary loss of control over the bladder. Incontinence is primarily treated through pharmaceuticals and surgery. Many pharmaceuticals do not adequately resolve the issue and can cause unwanted side effects; further, a number of surgical procedures have a low success rate and/or are not reversible. Similar treatment insufficiencies have likewise been noted for many of the other maladies previously mentioned.

As an alternative to conventional pharmaceuticals and/or invasive surgical procedures, neurostimulation has more recently been recognized as a viable treatment approach for many patients. By way of background, the organs involved in bladder, bowel, and sexual function receive much of their control via the second, third, and fourth sacral nerves, commonly referred to as S2, S3, and S4, respectively. Electrical stimulation of these various nerves has been found to offer some control over these functions. Several electrical stimulation techniques have been suggested, including stimulation of nerve bundles within the sacrum. Regardless, in order to consistently deliver electrical stimulation to the sacral nerve(s), certain anatomical obstacles must be addressed. The sacrum is a large, triangular bone situated at the lower part of the vertebral column, and at the upper and back part of the pelvic cavity. The spinal canal runs through the greater part of the sacrum. Further, the sacrum is perforated by the anterior and posterior sacral foramina though which the sacral nerves pass.

With the above anatomical description in mind, partial control over one or more of the functions (or dysfunctions) previously mentioned has been achieved by implanting a neurostimulation lead at or near the sacral nerves. As a point of reference, other nerve(s) or tissue can similarly be electrically stimulated to produce different effects. Relative to sacral nerve stimulation, however, the neurostimulation lead, having several stimulation electrodes, can be permanently implanted within and/or anteriorly beyond the sacral foramen at which the sacral nerve in question is anatomically located. Because the lead, and in particular the stimulation electrodes, must remain in operative proximity to the sacral nerve, the permanent lead (sometimes referred to as a "chronic lead") can be sutured within the patient's body to resist migration. In light of the invasive nature associated with this approach, minimally invasive neurostimulation leads have been developed, incorporating features proximal the electrodes that inhibit migration and/or retrograde dislodgement. Permanent leads of this type are typically somewhat sizable to not only present a sufficient number of electrodes, but to also better resist migration. Regardless, wire cabling from the lead is implanted within a subcutaneously formed tunnel and connected to a subcutaneously-implanted pulse generator. One example of such a system is available from Medtronic, Inc., of Minneapolis, Minnesota under the trade name InterStim®. Other chronic leads/systems are further described in U.S. Pat. Nos. 6,999,819; 6,971,393; and 6,847,849, each commonly assigned to the assignee of the present invention and the teachings of all of which are incorporated herein by reference.

Some patients may view the permanent neurostimulation lead and related pulse generator implantation described above as being a fairly traumatic procedure. Thus, efforts are conventionally made to ascertain in advance whether the patient in question is likely to receive benefit from sacral nerve stimulation. In general terms, the test stimulation procedure entails the temporary implantation of a neurostimulation lead in conjunction with an externally carried pulse generator or other power source. Once in place, the patient is exposed to neurostimulation over a trial period (e.g., 3-7 days) during which the patient can experience the sensation of nerve stimulation during various everyday activities, as well as recording the changes, if any, in the bodily dysfunction of concern (e.g., a patient experiencing urinary incontinence can maintain a voiding diary to record voiding behavior and symptoms with the stimulation). The record of events is then compared with a base line and post-test stimulation diaries to determine the effect, if any, of sacral nerve stimulation on the symptoms being experienced by the patient. If the test stimulation is successful, the patient and his/her clinician can make a better informed decision as to whether permanent implantation and long-term sacral nerve stimulation is a viable therapy option.

Temporary implantation of the neurostimulation lead is normally done in one of two manners. With one approach, sometimes referred to as a "staged implantation," a conventional, permanent or chronic neurostimulation lead is implanted at the desired sacral location, with the cable carrying the coiled conductor wiring being externally extended through the patient's skin and coupled to the pulse generator. While viable, this technique entails the use of surgical equipment normally employed to permanently implant the stimulation lead. By way of background, implantation of a permanent sacral nerve stimulation lead normally requires the use of a fairly large introducer (e.g., an elongated, 13 gauge tube), and the chronic stimulation lead has a fairly large diameter. While local and/or general anesthesia is available, some patients may be apprehensive to participate in a short-term test of this type in view of the size of the instrument(s)/stimulation lead.

To better address the reluctance of some patients to participate in the stimulation test procedure described above, a second technique has been developed that entails the use of a smaller diameter, more simplified neurostimulation lead intended to be implanted on only a temporary basis. In general terms, the temporary stimulation lead (sometimes referred to as a peripheral nerve evaluation lead or "PNE" lead) has a single electrode and is of sufficiently small diameter so as to be percutaneously inserted using a small diameter needle (e.g., a 20 gauge needle). Many patients are not overly threatened by a small diameter needle and thus are more likely to participate in the trial stimulation. The percutaneous test stimulation is similar to an epidural nerve block, except that the temporary lead is inserted and left in the patient's back during the trial. The end of the lead that remains on the outside of the patient's body is secured to the patient's skin with, for example, surgical tape. Upon conclusion of the trial stimulation, the lead is removed from the patient.

The accepted technique for delivering the PNE lead relative to the sacral nerves is to first percutaneously direct the small diameter needle to the sacral dorsal surface. Through various manipulations of the needle, a foramen of the sacrum is located. In this regard, the needle tip is electrically conductive and is periodically and/or continuously energized to assist in locating a foramen and the peripheral sacral nerve(s) associated therewith. As is known, when the energized needle tip is in close proximity to a sacral nerve, the patient will exhibit an involuntary bodily reaction (e.g., toe and/or foot movement). In connection with this foramen/sacral nerve location procedure, the needle establishes a pathway through the foramen conducive for subsequent placement of the PNE lead. Once a sacral nerve(s) has been located, energization of the needle tip is stopped and the clinician attempts to retain the needle, and in particular the tip of the needle, at the identified location. Subsequently, the PNE lead is coaxially disposed through a needle of the lumen and delivered distally therefrom. Once a portion of the PNE lead is forced distally through the needle and into the implantation site, the needle is proximally withdrawn over the lead body. While highly viable, this needle/lead exchange can be time consuming. Further, a possibility that the clinician may inadvertently move the needle relative to the desired implantation site prior to delivery of the lead body from the needle. Under these circumstances, then, it is possible for the lead body and in particular the electrode(s) carried thereby, to not be in operative proximity relative to the sacral nerve initially identified by the above-described needle placement process. As a result, the clinician may be required to repeat the entire procedure and/or be uncertain as to whether the PNE lead was properly located at the desired implantation site.

In addition, while the temporary simulation lead is highly capable of delivering the necessary stimulation energy throughout the evaluation period, it is possible that the lead may migrate. For example, any pulling or tugging on the proximal end of the lead body (from outside of the patient's body) could be directly communicated to the lead's electrode, thus creating a higher likelihood of electrode dislodgement and poor stimulation. Efforts have been made to address this concern, for example as described in U.S. Pat. No. 6,104,960, the teachings of which are incorporated herein by reference and assigned to the assignee of the present invention. In particular, a temporary neurostimulation lead is described as having a coiled configuration that better accommodates axial forces placed onto the lead body (e.g., tugging or pulling on the proximal end of the lead body). Any additional efforts to further minimize migration of the temporary neurostimulation lead would be well received, not only in the one exemplary context of peripheral sacral nerve electrical stimulation, but also for any other procedure in which an implantable medical electrical stimulation lead is used. Further, in an effort to provide a reduced size body for passage through a small diameter needle, conventional PNE-type leads incorporate only one electrode (i.e., a unipolar lead electrode), such that a return electrode (or ground pad) is typically applied to the patient's skin. The ground pad may cause the patient some discomfort, and in some instances can become dislodged or disconnected during the test period, thus preventing the test stimulation therapy from occurring.

In light of the above, a need exists for a system and method for delivering a medical electrical stimulator to a delivery site, such as a PNE lead to a sacral location, in a manner that does not require a complete needle-for-lead exchange. Other needs exist for bipolar PNE-type leads.

SUMMARY OF THE INVENTION

Some aspects in accordance with principles of the present invention relate to a system for providing medical electrical stimulation to bodily tissue of a patient. The system includes a lead assembly and a cannula. The lead assembly includes a lead body and a needle tip. The lead body has a distal section and a proximal section. The needle tip is formed of an electrically conductive material and defines a proximal segment, an intermediate segment, and a distal segment. The distal segment tapers in outer diameter from the intermediate segment, with the intermediate segment forming an abutment surface. With this construction, the distal section of the lead body is connected to the proximal segment of the needle tip in an electrically conductive fashion. The cannula includes a distal end, a proximal end, and a lumen. In this regard, the lead body is slidably disposed within the cannula lumen, with the distal end of the cannula being releasably connected to the needle tip adjacent the abutment surface such that upon final assembly, the distal segment of the needle tip extends distal the distal end of the cannula so as to define a needle probe. With this construction, the lead assembly can be delivered to a desired implantation site via manipulation of the cannula and/or energization of the needle tip, and the cannula can be removed from the lead body without requiring movement of the needle tip. In one embodiment, the needle tip and the cannula are sized to be percutaneously directed through a sacrum foramen to provide electrical stimulation to a sacral nerve. In other embodiments, the lead body forms an exposed electrode surface proximately spaced and electrically isolated from the needle tip such that the needle tip in the exposed electrode surface are operable to form a bipolar electrode assembly.

Other aspects in accordance with principles of the present invention relate to methods of providing electrical stimulation to a bodily tissue of a patient at a stimulation site. The method includes providing a delivery system including a lead assembly and a cannula. The lead assembly includes a lead body, having a distal section and a proximal section, and a needle tip formed of an electrically conductive material. In this regard, the needle tip defines proximal, intermediate, and distal segments, with the distal segment tapering in outer diameter from the intermediate segment, and the intermediate segment forming an abutment surface. Further, the distal section of the lead body is connected to the proximal segment of the needle tip in an electrically conductive manner. The cannula, in turn, has a distal end, a proximal end, and a lumen. With this construction, the lead body is slidably disposed within the cannula such that the distal end of the cannula abuts the abutment surface, and the distal segment of the needle tip extends distal the cannula. The needle tip is percutaneously delivered toward the stimulation site by applying a force onto the cannula. The needle tip is then positioned at the stimulation site. The cannula is proximately withdrawn from the lead body, with the proximal section of the lead body being external the patient. Finally, a stimulation energy is periodically applied to the needle tip via a power source electrically coupled to the lead body external the patient to electrically stimulate the stimulation site. In one embodiment, the stimulation site relates to a sacral nerve, such that percutaneous delivery of the needle tip includes locating a sacrum foramen and inserting the needle tip into the sacrum foramen. In other embodiments, proximally withdrawing the cannula from the lead body includes applying an axial force onto the needle tip via a pushing force applied to the proximal section of the lead body.

DETAILED DESCRIPTION OF THE INVENTION

Figure 1:
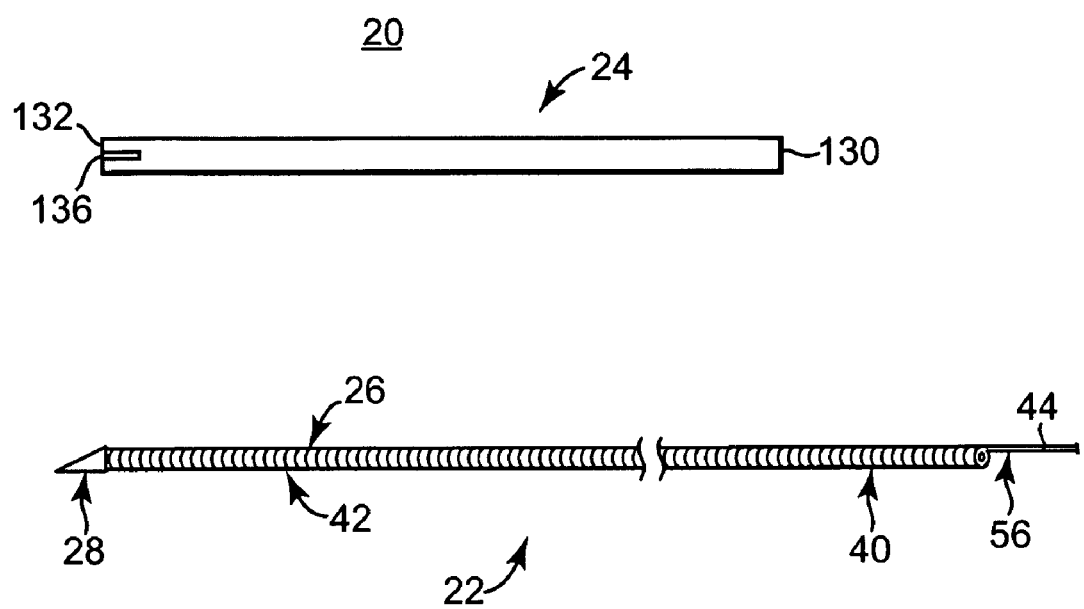
FIG. 1 is an exploded plan view of a system for providing medical electrical stimulation in accordance with principles of the present invention.

One embodiment of a system 20 for use in providing medical electrical stimulation to bodily tissue to a patient, such as a portion of the patient's nervous system, is shown in simplified form in FIG. 1. The system 20 includes a lead assembly 22 and a cannula 24. Though not shown, the system 20 can include additional components, such as a power source (e.g., a pulse generator such as a Model 3625 InterStim® Test Stimulator available from Medtronic, Inc., of Minneapolis, MN.). Regardless, details on the various components are provided below. In general terms, however, the lead assembly 22 includes a lead body 26 and a needle tip 28. The lead body 26 is sized to be slidably received within the cannula 24, with at least a portion of the needle tip 28 extending distally therefrom. In this regard, the cannula 24 is releasably connected to the needle tip 28 such that during use, the cannula 24 can be manipulated to percutaneously delivery the needle tip 28/lead body 26 to a desired implantation site, for example in close proximity to one or more nerves. Once located, the cannula 24 can be proximally withdrawn from the lead body 26 with a position of the needle tip 28 remaining unchanged. In one embodiment, the system 20 is adapted for use in performing a sacral peripheral nerve stimulation, whereby the cannula 24 and the needle tip 28 are appropriately sized for percutaneous insertion into a sacral foramen.

The lead body 26 defines a proximal section 40 and a distal section 42. In one embodiment, the proximal section 40 is adapted for electrical coupling to a power source, and thus can include one or more connector pins 44. Further, the lead body 26 is preferably electrically conductive so as to conduct energy from the proximal section 40 to the distal section 42, and thus to the needle tip 28 via electrical connection between the distal section 42/needle tip 28 as described in greater detail below.

In one embodiment, the lead body 26 is configured to be flexible, exhibiting longitudinal strain relief such that any pulling or tugging on the proximal section 40 is not directly translated to the distal section 42, and in particular to the needle tip 28 (via the needle tip 28/distal section 42 attachment as described below). With this in mind, and with reference to FIG. 2A, in one embodiment, the lead body 26 includes a wire 50 wound to form a wound coil. The wire coil 50 can be closely wound as shown, or alternatively a longitudinal spacing can be defined between individual winding. The wound coil configuration of the wire 50 exists along at least the distal section 42, but in some embodiments further is formed at or along the proximal section 40 (FIG. 1). The wire 50 is formed of an electrically conductive metal such as stainless steel (e.g., SST 316L stainless steel multi filament wire, MP35N alloy, etc.).

Figure 2A:
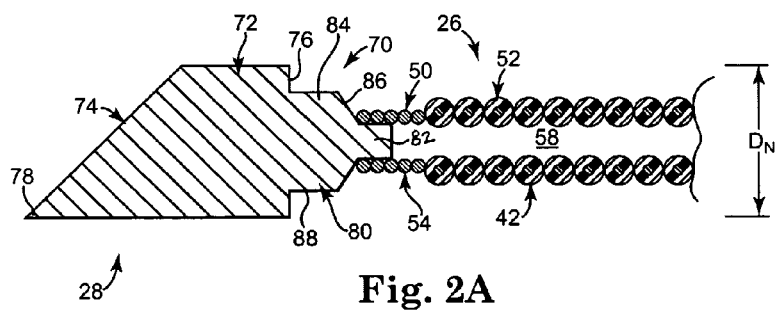
FIG. 2A is an enlarged cross-sectional view of a portion of a lead assembly associated with the system of FIG. 1.

An electrically non-conductive material or insulator 52 is disposed, formed, or coated over a majority of the wire 50 to electrically insulate the wire 50. In one embodiment, the non-conductive material 52 is ETFE (a polymer of tetrafluoroethylene and ethylene), although other materials such as PTFE, polyurethane, fluoropolymers, silicone rubber, polyester, etc., are also useful. The non-conductive material 52 is not coated to the wire 50 at a distal end portion 54 and a proximal end portion 56 (FIG. 1) thereof. With this configuration, then, the proximal end portion 56 can readily establish electrical communication with the power source (not shown) whereas the distal end portion 54 can readily establish electrical connection with the needle tip 28 as described below. Alternatively, the distal end portion 54 (and in some embodiments, the proximal end of portion 56) of the wire 50 can have the non-conductive material 52 coated on an exterior side thereof, while an interior side remains electrically exposed. Similarly, while the wire 50 is shown in FIG. 2A as being encompassed by the non-conductive material 52, in other embodiments, the non-conductive material 52 is applied to a lesser extent (e.g., only to an exterior of the wound wire coil 50). Regardless, in one embodiment, the lead body 26 forms a center passage 58 sized, for example, to receive a stylet (not shown) as described in greater detail below.

In one embodiment, the lead body 26 is akin to a PNE lead having a reduced-sized outer diameter (as compared to a conventional, permanent, or chronic stimulation lead), for example, of not more than 0.05 inch, more preferably not more than 0.04 inch, and even more preferably not more than 0.03 inch, and in one embodiment on the order of 0.025 inch. With this configuration, the lead body 26 can pass through a small diameter tube. Thus, and as described in greater detail below, this configuration of the lead body 26 facilitates sizing of the cannula 24 (FIG. 1) to also have a relatively small diameter lumen such that the cannula 24 can, in some embodiments, be a 19 or 20 gauge tube. In other embodiments, however, the lead body 26 can have a larger outer diameter.

With the above description of the lead body 26 in mind, one embodiment of the needle tip 28 is shown in greater detail in FIG. 2A. In general terms, the needle tip 28 is defined by a proximal segment 70, an intermediate segment 72, and a distal segment 74. In one embodiment, the segments 70-74 are integrally formed such that the needle tip 28 is a homogenous body. Alternatively, one or more of the segments 70-74 can be separately formed and subsequently assembled. Regardless, in one embodiment, the needle tip 28 is formed of a hardened, electrically conductive material such as stainless steel, stainless steel platinum, PtIr, MP35N, etc. In general terms, the proximal segment 70 is configured for attachment to the distal section 42 of the lead body 26 as well as for releasable connection to the cannula 24 (FIG. 1). The intermediate segment 72 extends from the proximal segment 70, and defines an abutment surface 76 for receiving the cannula 24 in an abutting relationship as described in greater detail below. The distal segment 74 extends from the intermediate segment 72, tapering in outer diameter to a tip end 78 that can be sharp in some embodiments.

In one embodiment, the proximal segment 70 includes a post 80 adapted to facilitate a permanent attachment and electrical connection with the lead body 26, as well as selective or releasable engagement with the cannula 24. For example, the post 80 can include a proximal region 82, a distal region 84, and a shoulder 86 defined at a transition of the proximal region 82 to the distal region 84. An outer diameter of the proximal region 82 is less than an outer diameter of the distal region 84 in one embodiment, with the proximal region 82 being sized in accordance with a diameter of the center passage 58 defined by the wire/coil 50. With this configuration, then, the post 80 is received with the wire coil 50 along the proximal region 82 to effectuate coupling therebetween, with distal end portion 54 of the wire 50 nesting against the shoulder 86. A weld, crimp, or component is formed to permanently affix the resultant joint in an electrically conductive manner. In other embodiments, the proximal region 82 of the post 80 can form an aperture (not shown) within which the distal section 42 of the wire 50 is received and attached (e.g., weld, crimp, etc.). A wide variety of other assembly techniques are also contemplated. Regardless, in one embodiment, the distal region 84 of the post 80 has a diameter commensurate with an inner diameter of the cannula 24 as described in greater detail below. To this end, in one embodiment, the distal region 84 forms or includes a diameter 88 (referenced generally in FIG. 2A) sized to be slidably received within a corresponding component of the cannula 24 as described below in press fit-type relationship. Alternatively, the post 80 can have other features that facilitate selective connection with the cannula 24, such as a protrusion (not shown) sized to be selectively received within an undercut in the cannula 26.

The intermediate segment 72 defines a maximum diameter $D_N$ of the needle tip 28. Thus, in one embodiment, the abutment surface 76 is defined as a radially outward extension relative to the proximal segment 70, such that the abutment surface 76 serves as a radial face. Commensurate with the above description of the lead body 26 otherwise having, in some embodiments, a reduced-sized outer diameter, in one embodiment, the maximum needle tip diameter $D_N$ is less than 0.06 inch, more preferably less than 0.05 inch, and even more preferably on the order of 0.037 inch (+/−0.005 inch). In other embodiments, however, the maximum needle diameter $D_N$ can be greater than 0.06 inch.

Finally, the distal segment 74 tapers in diameter in extension from the intermediate segment 72 to the tip end 78. In this regard, a length, degree of taper, and surface configuration/sharpness of the distal segment 74 can vary from the one embodiment of FIG. 2A. For example, while the tip end 78 is shown as being offset from a center line of the needle tip 28, in other embodiments, the distal segment 74 can have a conical shape, such that the tip end 78 is approximately centered relative to the intermediate segment 72. Further, the distal segment 74, as well as the needle tip 28 as a whole, can have other configurations suited for a particular procedure to be performed (e.g., the needle tip 28 can be shaped and/or sized in a manner to optimally interface with bodily materials expected to be encountered during a particular procedure).

Figure 2B:
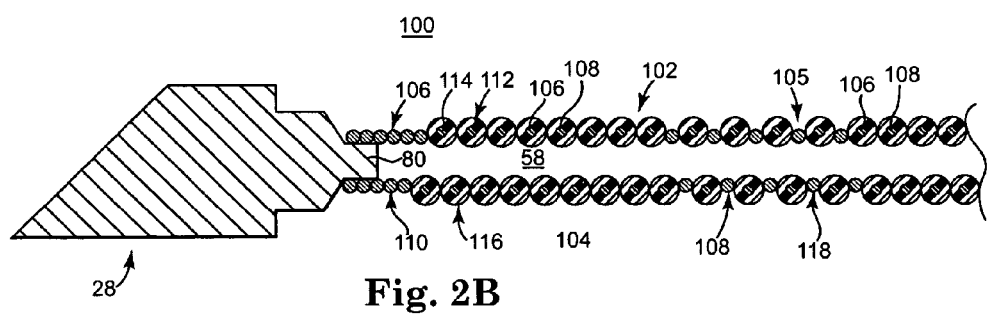
FIG. 2B is an enlarged cross-sectional view of an alternative embodiment lead assembly in accordance with principles of the present invention.

In accordance with the one embodiment lead assembly 22 of FIG. 2A, the lead body 26 serves to conduct electrical energy from the proximal section 40 (otherwise electrically coupled to, for example, a power source such as a pulse generator) to the distal section 42; in turn, the so-conducted energy is conducted to the needle tip 28. The electrically conductive nature of the needle tip 28 exteriorly conducts the applied energy to, for example, stimulate a nerve(s) in relatively close proximity to the needle tip 28. Thus, the lead assembly 22 provides a unipolar probe such that a return electrode (not shown), for example a ground pad, may also be required to perform an electrical stimulation procedure. Alternatively, the lead assembly 22 can be configured to provide a bipolar electrode assembly. For example, FIG. 2B illustrates a portion of an alternative embodiment lead assembly 100 including a lead body 102 and the needle tip 28. The lead body 102 is akin to the lead body 26 (FIG. 2A) previously described, and is defined by a proximal section (not shown) and a distal section 104. The distal section 104 is configured for attachment to the needle tip 28 as previously described. However, with the embodiment of FIG. 2A, the lead body 102 forms an exposed electrode surface 105 (referenced generally), and includes first and second wires 106, 108 that are coaxially wound to one another in defining wound coils.

The first wire/coil 106 is akin to the wire/coil 50 (FIG. 2A) previously described and provides an electrical connection to the needle tip 28. In this regard, apart from a distal end portion 110 and a proximal end portion (not shown) thereof, an entirety of the first wire 106 is coated or encompassed with an electrically non-conductive material 112 for the reasons previously described. The second wire 108 is similar formed of an electrically conductive material (e.g., stainless steel such as SST 316L stainless steel multi filament wire), terminating at a distal end 114. As shown in FIG. 2B, the first wire 106 extends distal the distal end 114 of the second wire 108 in one embodiment. Regardless, the second wire 108 is coated or otherwise encompassed by a non-conductive material 116 except at a proximal end (not shown) and an uncovered region 118 (referenced generally). With this configuration, then, the uncovered region 118 defines the exposed electrode surface 105. By way of reference, FIG. 2B illustrates individual windings of the first wire/coil 106, otherwise covered by the non-conductive material 112, being interposed between individual windings of the second wire/coil 108 along the covered region 118. The first and second wires 106, 108 are thus electrically isolated from one another.

With the above configuration, the needle tip 28 and the exposed electrode surface 105 can operate as a bipolar electrode assembly with energy being applied to the needle tip 28 via the first wire 106, and the exposed electrode surface 105 providing a current return path via the second wire/coil 108 as otherwise electrically isolated from the first wire/coil 106. Alternatively, the lead assembly 100 can assume a variety of other configurations capable of providing a bipolar electrode assembly.

Figure 3:
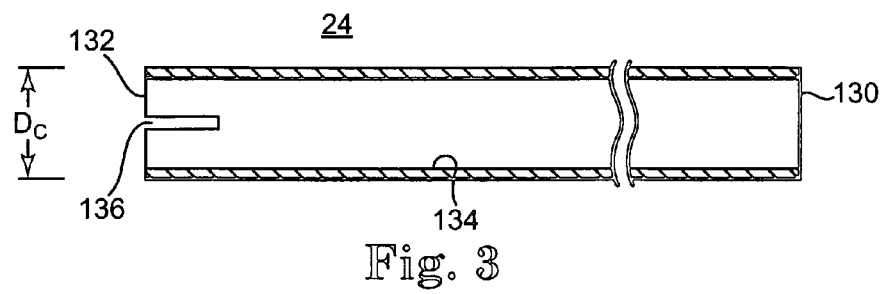
FIG. 3 is an enlarged, cross-sectional of a cannula of the system of FIG. 1.

Returning to FIG. 1, and with additional reference to FIG. 3, the cannula 24 defines a proximal end 130, a distal end 132, and a lumen 134 extending between the ends 130, 132. In one embodiment, the cannula 24 is a thin wall metal tube akin to a 20 gauge needle commonly used in performing a percutaneous sacral foramen access procedure, for example a 19 gauge or 20 gauge thin wall metal needle (e.g., 20 gauge foramen needles available from Medtronic, Inc., of Minneapolis, MN. under product numbers 041828 or 041829), except that the distal end 132 does not form a needle or sharpened tip. Instead, the distal end 132 is relatively flat, as shown in FIG. 3. Regardless, an outer diameter $D_C$ of the cannula 24 approximates the maximum outer diameter $D_N$ (FIG. 2A) of the needle tip 28 (FIG. 2A) (e.g., a difference between the diameters $D_C$ and $D_N$ is not greater than 0.01 inch in one embodiment). Further, a diameter of the lumen 134 approximates a diameter of the needle tip post 80 (FIG. 2A), with a thickness of the cannula 24 wall best being sized to interface with the needle tip 28 as described below. Regardless, the lumen 134 is sized to slidably receive the lead body 26, with the cannula 24 having a length that is less than a length of the lead body 26. Further, in one embodiment, the cannula 24 forms one or more slots 136 extending proximally from the distal end 132. The slot(s) 136 provides the distal end 132 with a spring-like attribute (thus promoting a slight interference fit with the needle tip 28). Alternatively, the cannula 24 can assume a variety of other configurations appropriate for facilitating a desired interface with the needle 28; thus, for example, the slots 136 need not be provided. In one embodiment, the cannula 24 is preferably electrically insulated with an appropriate, non-conductive coating (e.g., a parylene coating) along its outer surface.

Figure 4A:
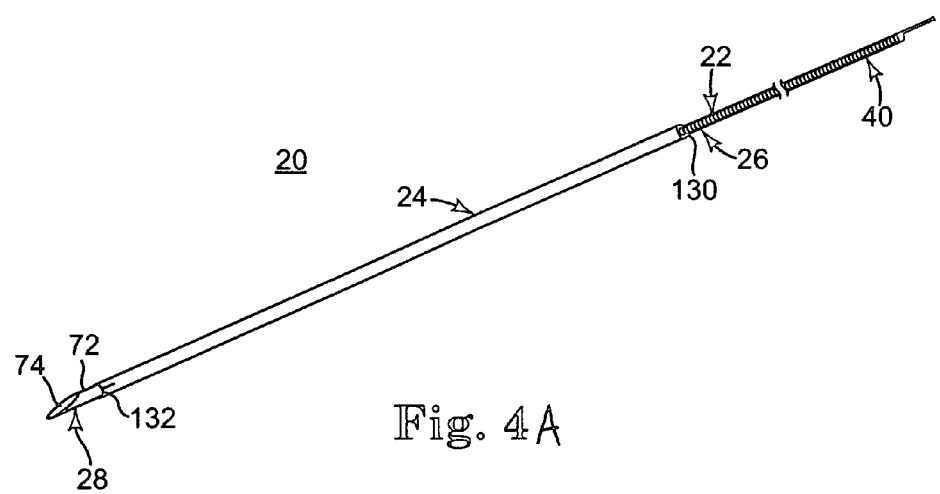
FIG. 4A is a perspective view of the system of FIG. 1 upon final assembly.
Figure 4B:
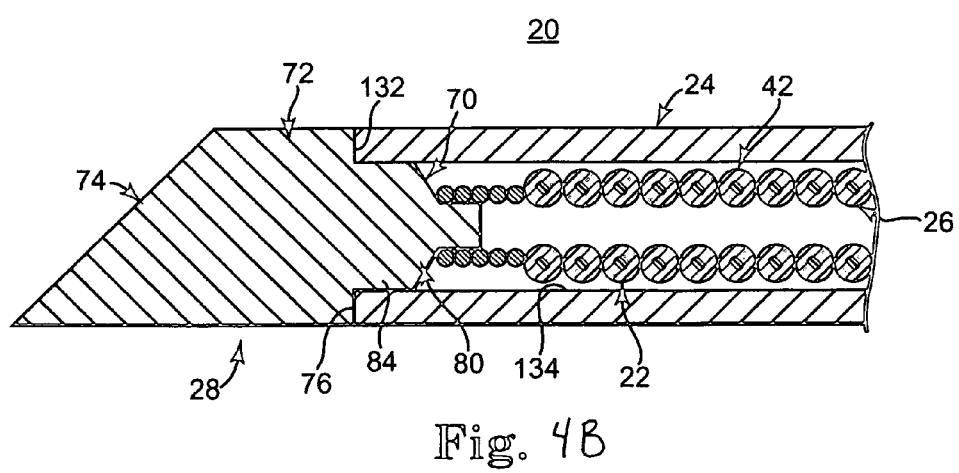
FIG. 4B is a cross-sectional view of a portion of the assembly of FIG. 4A.

One embodiment of the assembled system 20 is provided in FIGS. 4A and 4B. The lead assembly 22 is assembled to the cannula 24 such that the lead body 26 is slidably disposed within the cannula lumen 134, with the proximal section 40 of the lead body 26 extending proximally from the proximal end 130 of the cannula 24. Conversely, the needle tip 28 is releasably connected to the cannula 24 such that at least a portion of the needle tip 28 (e.g., the intermediate and distal segment 72, 74) extend distal the distal end 132 of the cannula 24.

As best shown in FIG. 4B, upon final assembly, a slight interference fit is provided between the cannula 24 and the distal region 84 of the post 80. In this regard, the slots 136 (FIG. 3) provide the cannula 24 with a spring-like attribute such that the distal region 84 can have a diameter slightly greater than a diameter of the cannula lumen 134; the slots 136 allow the cannula 24 to slightly expand in diameter to thus engage the post 80 in a releasable fashion. The releasable connection of the cannula 24 to the needle tip 28 can be further enhanced by a low bonding strength adhesive and/or a sticky adhesive material that dissolves in the presence of bodily fluids. Additionally, other mechanisms can be provided with the system 20 to facilitate releasable engagement between the cannula 24 and the needle tip 28. Regardless, in one embodiment, the distal end 132 of the cannula 24 bears against or abuts the abutment surface 76 formed by the needle tip 28.

In one embodiment, the needle tip 28 can be released from the cannula 24 via an axial force imparted onto the proximal segment 70 of the needle tip 28 in a distal direction relative to the cannula 24. For example, an axial pushing force can be applied to the proximal section 40 (FIG. 4A) of the lead body 26 while the cannula 24 is held in a stationary position and/or is proximally retracted relative to the lead body 26. Regardless, the lead body 26 translates this axial force to the distal section 42, and thus onto the needle tip 28 to effectuate separation of the needle 28 from the cannula 24. In this regard, one or both of the lead body 26 and/or the cannula 24 can include a plunger-type handle (not shown) at proximal ends thereof to enhance a user's ability to manually effectuate this separation. With this in mind, in one embodiment and regardless of an exact configuration, releasable assembly of the cannula 24 to the needle tip 28 is characterized by a user being able to manually effectuate separation of the needle tip 28 from the cannula 24 via various manual manipulations performed at a proximal side of the system 20 (and thus outside of the patient's body during use). Alternatively, and/or in addition, a stylet (not shown) can be inserted through the central passage 58 of the lead body 26 and manipulated proximal the cannula 24 to provide an axial force onto the proximal segment 70 of the needle tip 28.

Figure 5A:
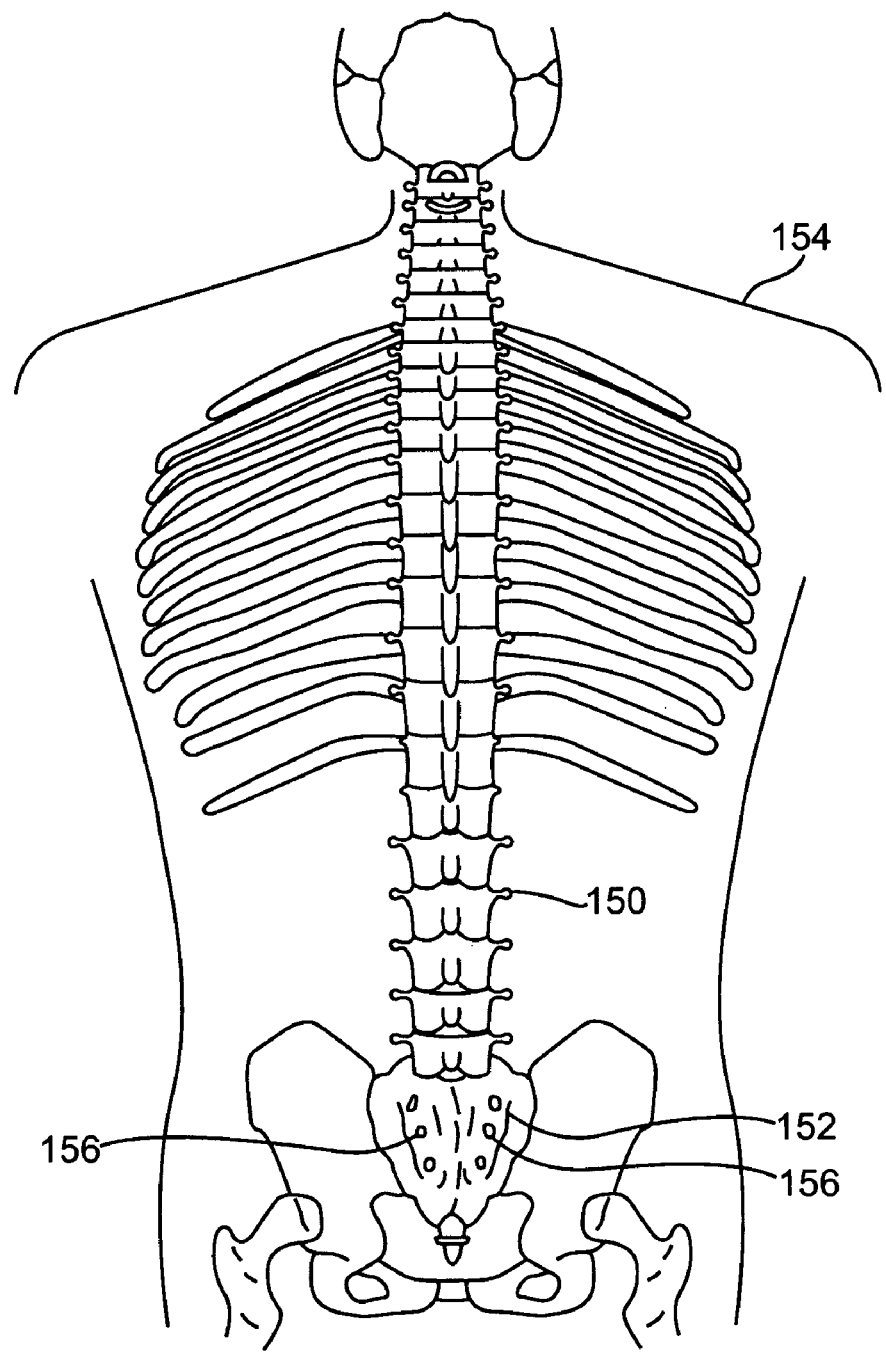
FIG. 5A is a posterior view of a spinal column of a patient, showing a location of a sacrum relative to an outline of the patient's body.
Figure 5B:
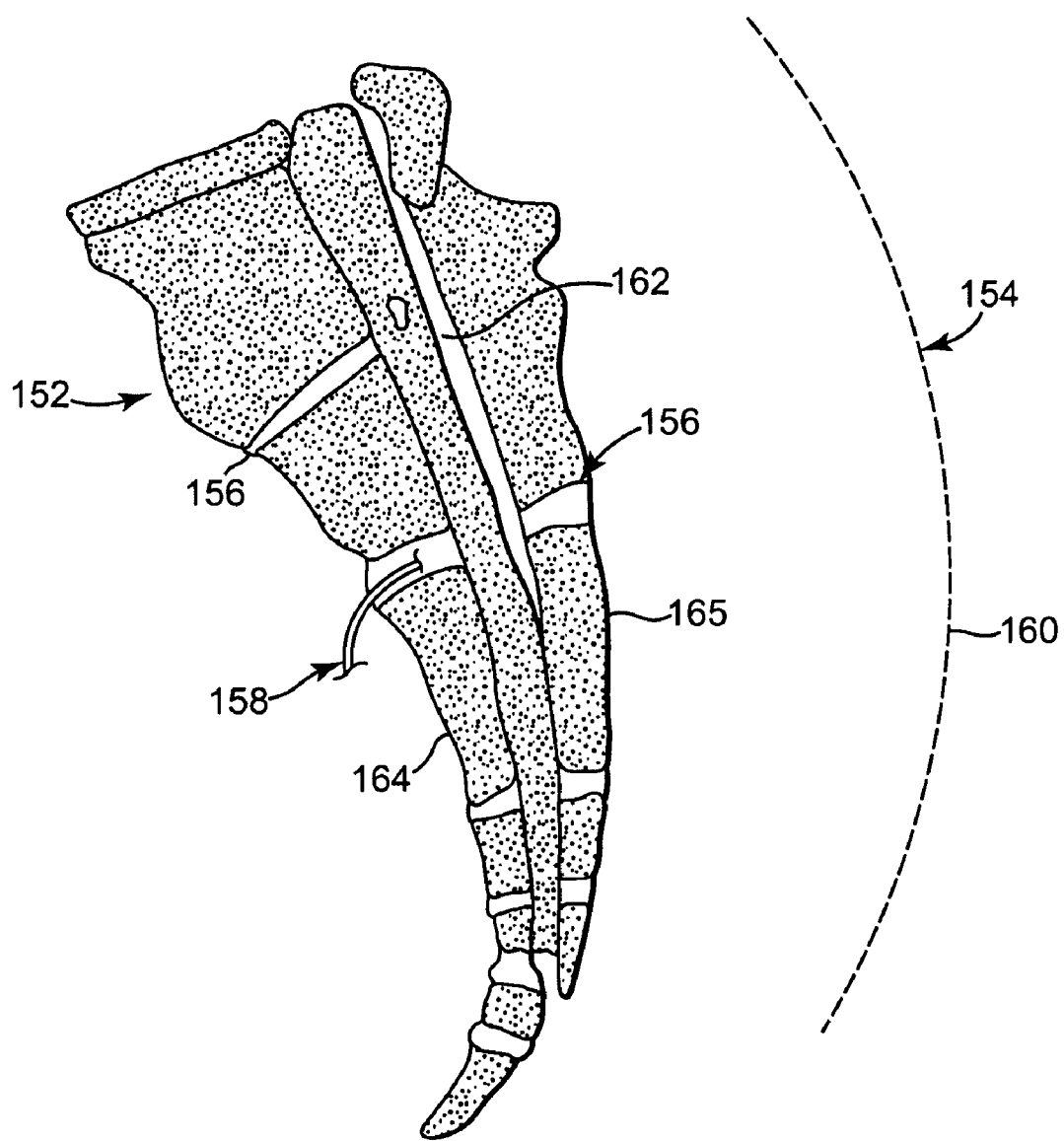
FIG. 5B is a simplified sectional view of a human anatomy in a region of the sacrum.

Returning to FIG. 1, the system 20 in accordance with principles of the present invention can be utilized to provide medical electrical stimulation to a wide variety of bodily structures via a percutaneous approach in conjunction with an external power source. For example, the system 20 can be deployed to stimulate one or more nerves of the nervous system. Alternatively, the system 20 can be used in other applications requiring electrical stimulation, such as procedures to rehabilitate muscle dysfunction by neuromodulation (e.g., functional electrical stimulation) of muscular behavior. In one embodiment, however, the system 20 is employed to provide electrical stimulation to a sacral nerve(s), for example as part of a peripheral sacral nerve simulation test or evaluation. With respect to this one exemplary application, FIG. 5A provides a posterior view of a spinal column 150 showing a location of a sacrum 152 relative to an outline of a patient's body 154. As shown, the sacrum 152 has a series of holes or foramen 156 therethrough. Each foramen 156 provides access to sacral ventral nerves (not shown). This relationship is further illustrated in FIG. 5B whereby sacral nerves (a peripheral sacral nerve of which is illustrated schematically and generally referenced at 158) extend along the sacrum 152, generally opposite a dorsal surface 160 of the patient's body 154, and through or from a sacral canal 162. FIG. 5B further illustrates a pelvic surface 164 and a dorsal surface 165 of the sacrum 152.

Figure 6:
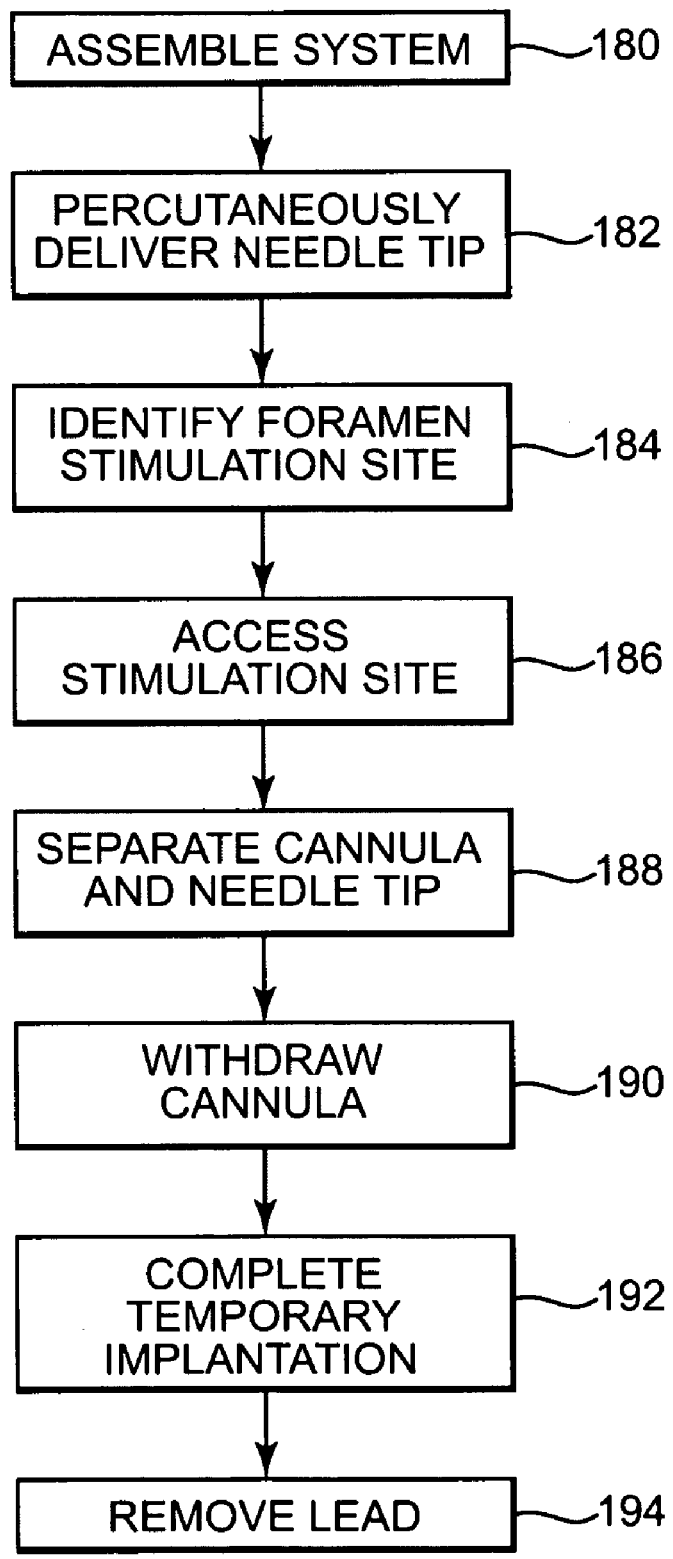
FIG. 6 is a flow diagram relating to a method of delivering an electrical stimulation to a portion of a patient's nervous system.
Figure 7A:
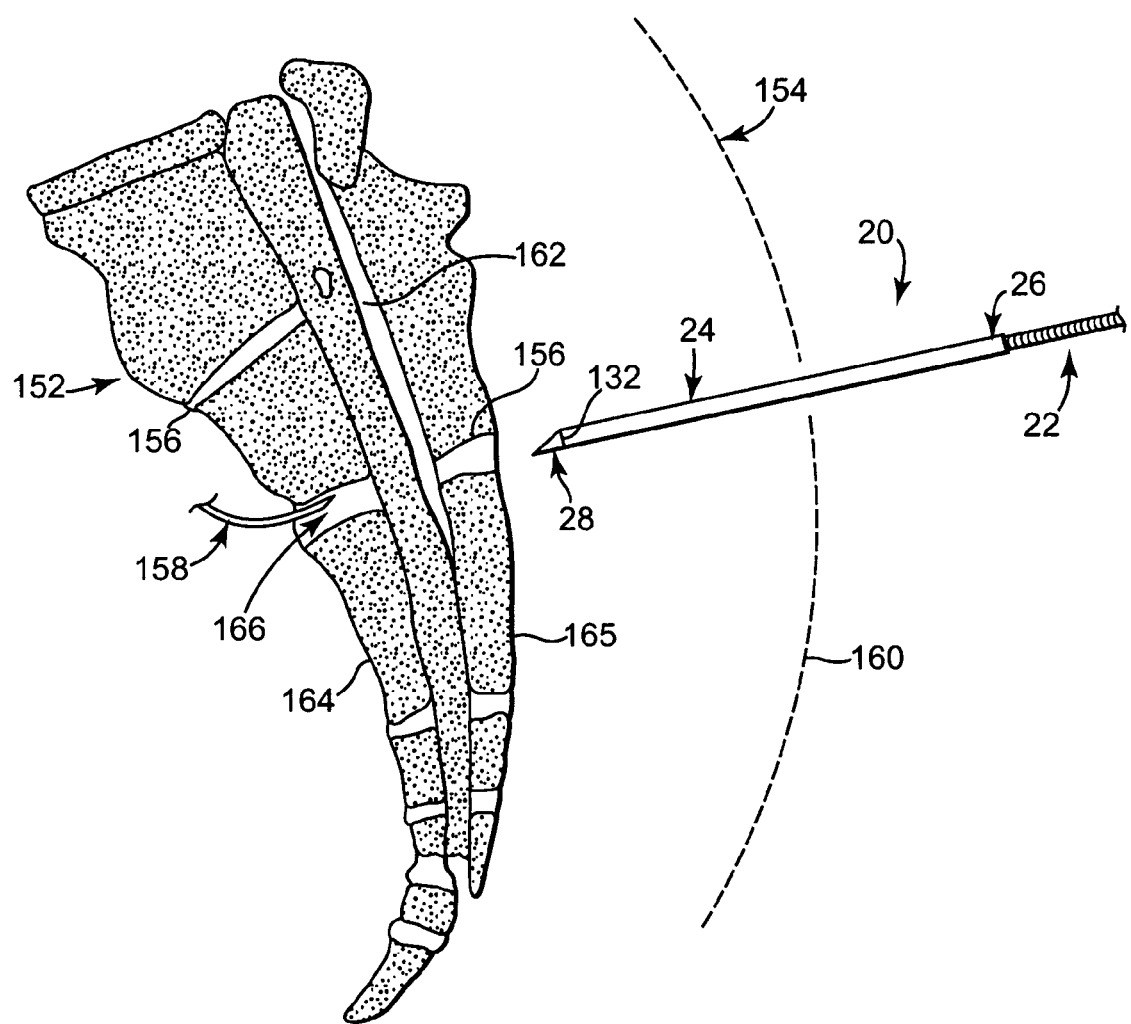
FIG. 7A-7D illustrate delivery of a stimulation lead to a sacrum of a patient in accordance with principles of the present invention.

With the above anatomical description in mind, one method of using the system 20 to provide medical electrical stimulation to at least one of the sacral nerves 158 in accordance with principles of the present invention is provided by the flow diagram of FIG. 6, in conjunction with the views of FIGS. 7A-7D. As a point of reference, while the foregoing description relates to the system 20 incorporating the unipolar lead assembly 22 configuration of FIG. 2A, the methodology is equally applicable using the bipolar lead assembly 100 (FIG. 2B). Regardless, at step 180, the system 20 is assembled, with the lead body 26 being slidably disposed within the cannula lumen 134, and the needle tip 28 extending distally from the distal end 132 of the cannula 24 as shown and described previously in FIG. 4B, with the needle tip 28 being releasably connected to the cannula 24. Once assembled, the needle tip 28 is percutaneously delivered proximate the sacrum 152 as shown in FIG. 7A via manual manipulation of the cannula 24 at step 182. In general terms, an insertion (or forward or distal) force applied to the cannula 24 is translated onto the needle tip 28 via the distal end 132/abutment surface 76 interface (FIG. 4B). Thus, the cannula 24 provides a relatively rigid body for directing the needle tip 28, and thus the flexible lead body 26, toward the sacrum 152.

At step 184, a desired sacral foramen 156 is identified using conventional techniques. For example, the clinician can identify an approximate location of the foramen 156 using various visualization techniques and/or by attempting or repeatedly attempting to insert the needle tip 28 through the foramen 156 based upon the clinician's estimation of where the foramen 156 is spatially located.

Figure 7B:
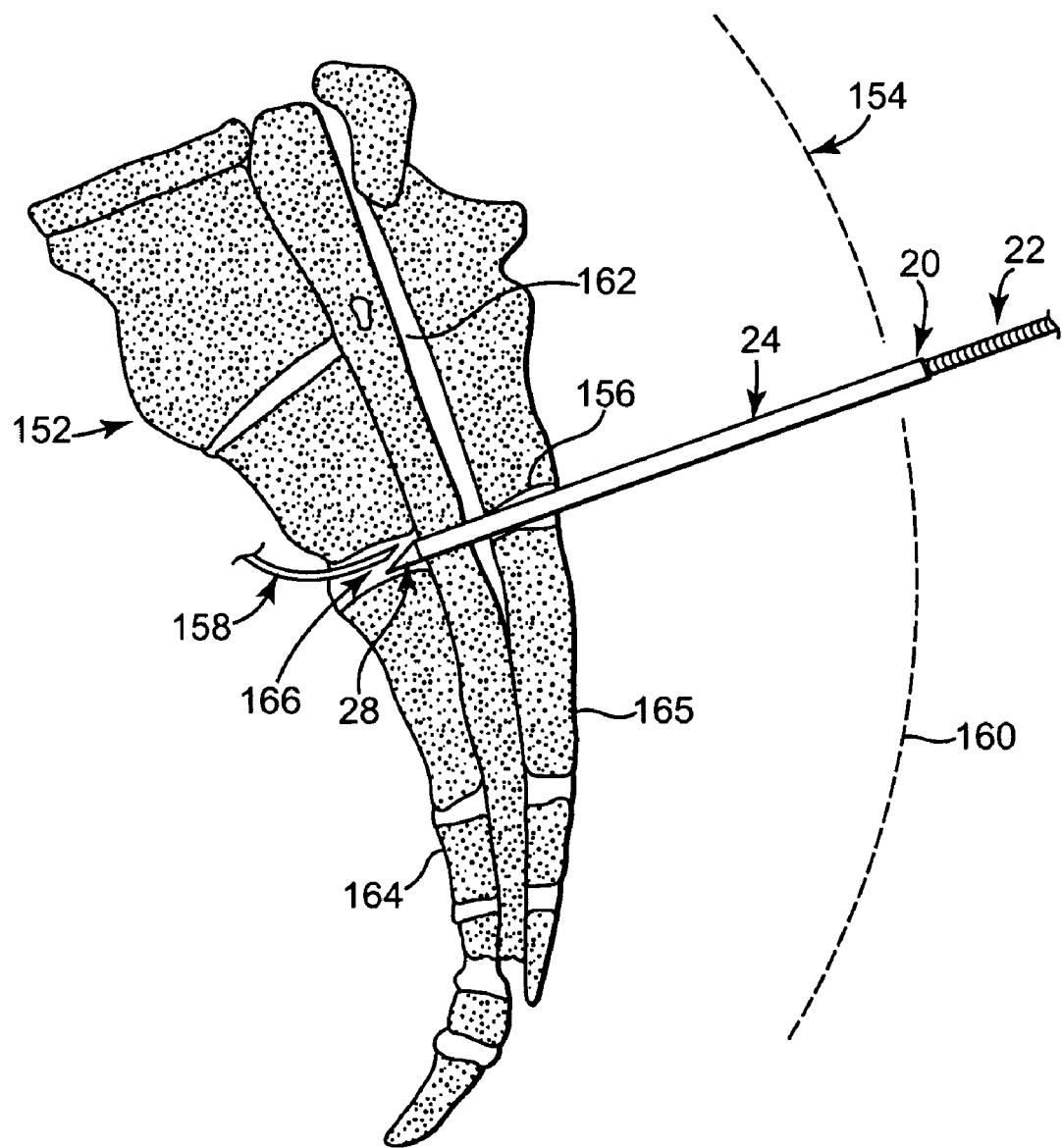

Once the desired foramen 156 has been located, at step 186, a desired implantation location or stimulation site 166 (referenced generally in the Figures) is obtained. In general terms, the desired implantation location 166 is characterized by the needle tip 28 being in operative proximity relative to one or more sacral nerve(s) 158 such that electrical energy applied to the needle tip 28 stimulates the sacral nerve 158. Thus, for example, the stimulation site 166 can be obtained by periodically or continuously applying electrical energy to the needle tip 28 via a power source (e.g., a pulse generator) electrically coupled to the proximal section 40 of the lead body 26. As previously described, electrical energy is conducted through the lead body 26 to the needle tip 28. Upon observing a physical reaction in the patient to the stimulation energy (e.g., movement of the patient's toe(s), foot, etc.), the clinician can determine that the needle tip 28 is in an operatively proximate position, and thus at the stimulation site 166. By way of reference, with the one embodiment system 20, a return electrode or ground pad (not shown) is secured to the patient's skin so as to facilitate delivery of the stimulation energy via the needle tip 28. Alternatively, where the lead assembly 22 is of a bipolar configuration (e.g., the lead assembly 100 of FIG. 2B), a ground or return pad is not necessary. Regardless, FIG. 7B illustrates the needle tip 28 being positioned at the stimulation site 166.

Figure 7C:
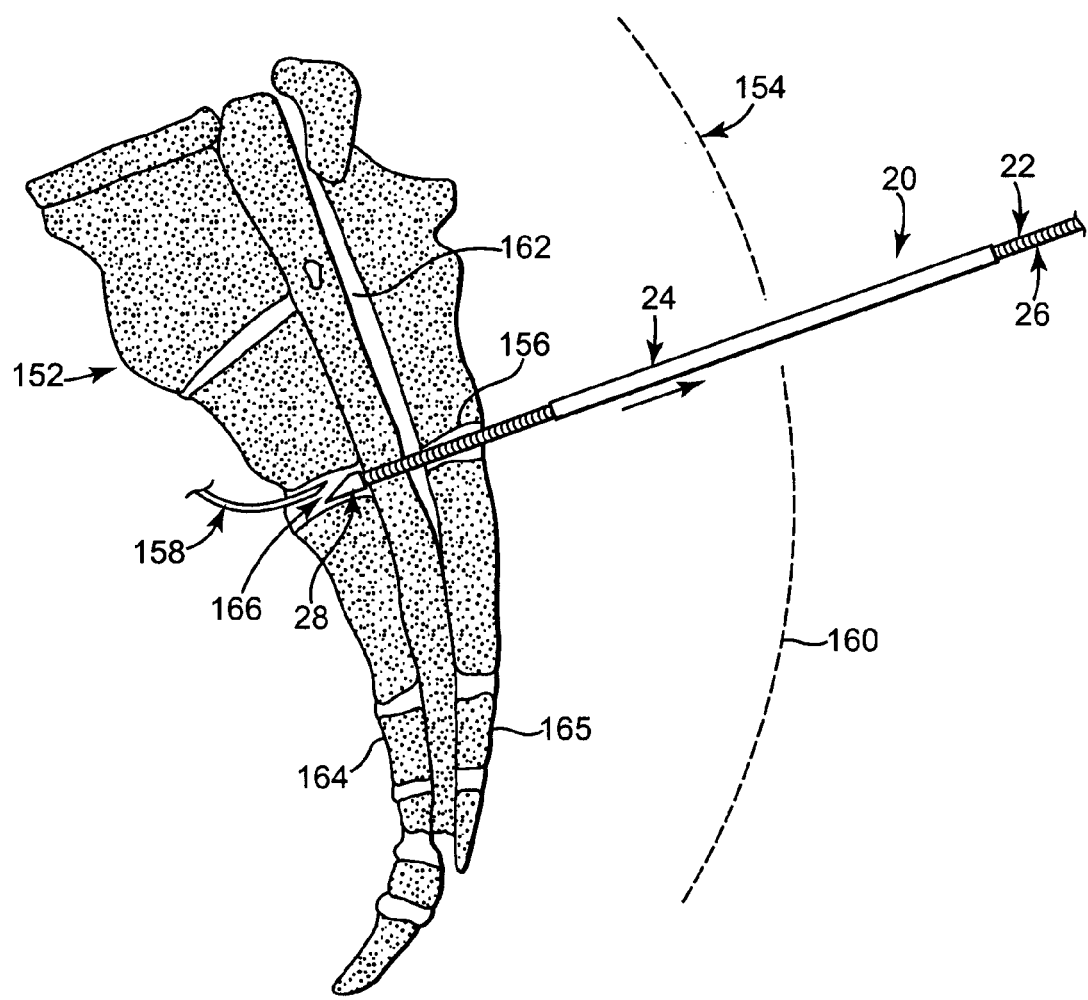

At step 188, implantation of the lead assembly 22 is completed by first separating the cannula 24 from the needle tip 28. As previously described, this separation can be achieved a variety of fashions. For example, an axial force can be imparted onto the needle tip 28 via a pushing force applied to the proximal section 40 of the lead body 26 and/or the cannula 24 can be pulled proximally relative to the needle tip 28, again via a pulling force applied external the patient. Following separation of the cannula 24 from the needle tip 28, at step 190 the cannula 24 is proximally withdrawn over and from the lead body 26 as shown in FIG. 7C. In this regard, steps 188 and 190 are characterized by the needle tip 28 remaining stationary or approximately stationary relative to the stimulation site 166 and the sacral nerve 158 that is otherwise in operative proximity to the needle tip 28. Thus, once the needle tip 28 has been desirably positioned, the clinician need not alter this position to complete the implantation procedure.

At step 192, temporary implantation of the lead assembly 22 is completed, for example, by securing (e.g., surgically taping a portion of the lead body 26 external the patient's body 154 to the patient). Further, an external power source (e.g., an external pulse generator) is or remains electrically connected to the proximal section 40 of the lead body 26 and is otherwise carried by the patient.

Figure 7D:
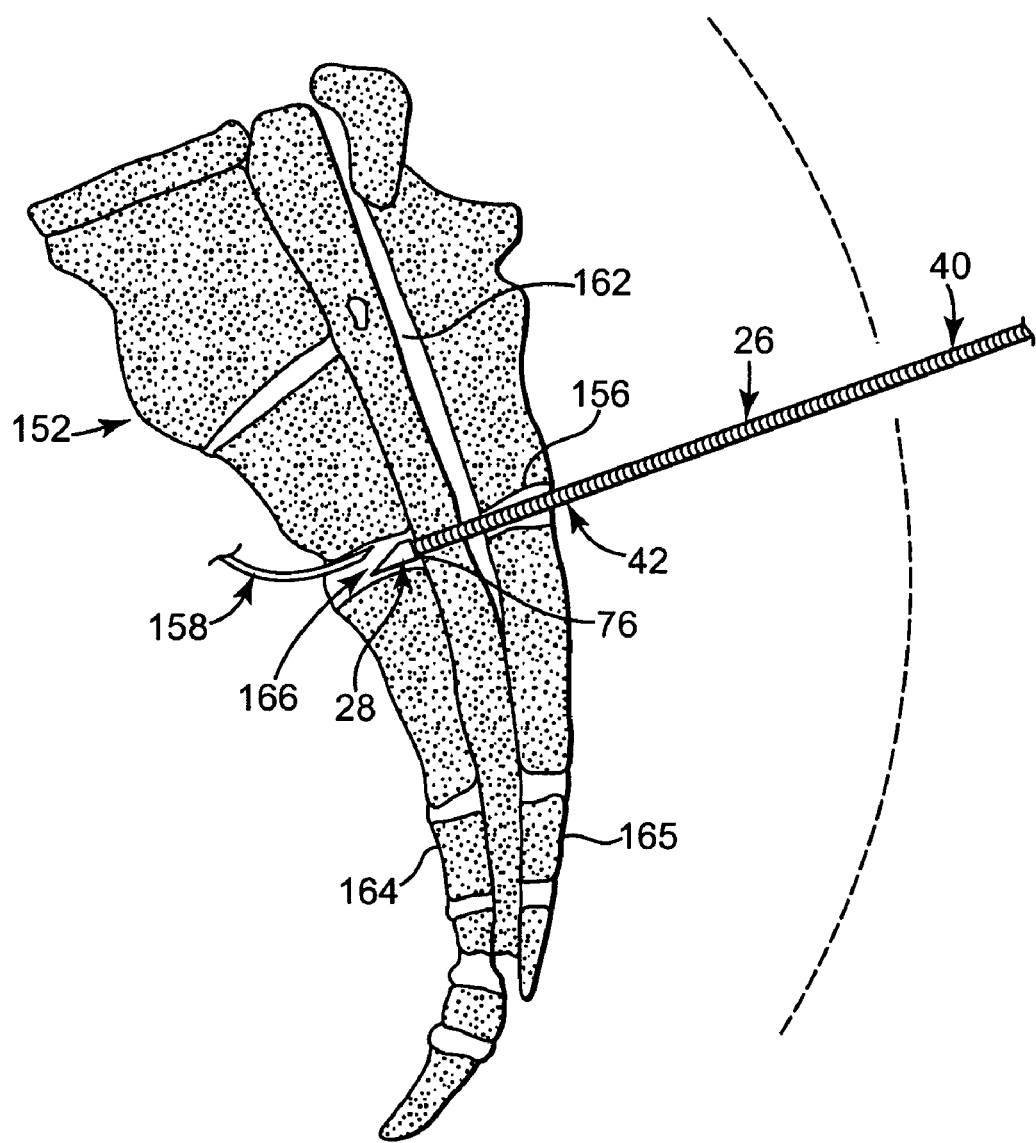

Following implantation, and as shown in FIG. 7D, the lead assembly 22 resists migration from the stimulation site 166. For example, the abutment surface 76 inhibits axial dislodgement of the needle tip 28/lead body distal section 42 back through the foramen 156. Further, in accordance with one embodiment, the coiled nature of the lead body 26 provides longitudinal strain relief such that any pulling or tugging on the proximal section 40 of the lead body 26 will not be automatically translated to the needle tip 28.

In one embodiment in which the system 20 is used in connection with a sacral peripheral nerve stimulation test, following the temporary implantation steps described above, the patient can then resume a day-to-day lifestyle over a test period (e.g., 3-7 days), during which the external power source (not shown) cause the needle tip 28 to periodically electrically stimulate the sacral nerve 158. Based upon the patient's response to this electrical stimulation over the test period, a decision can be made as to whether the patient is an appropriate candidate for receiving a permanently-implanted stimulation system. Once again, however, stimulation of a peripheral sacral nerve is but one procedure with which the system of the present invention is useful. Following completion of the stimulation procedure, the needle tip 28/lead body 26 is removed from the patient's body 154 at step 194, such as by applying a gentle pulling force on to the proximal section 40 of the lead body 26.

Figure 8:
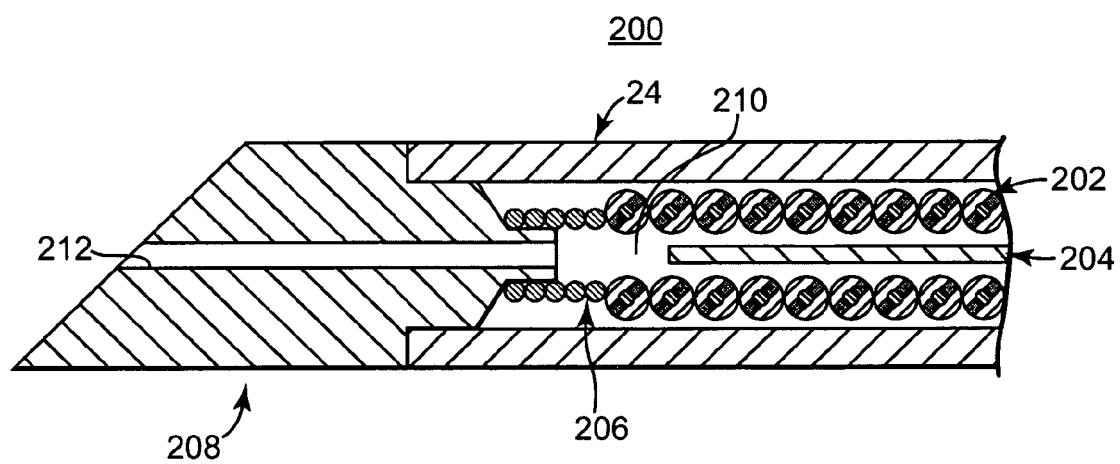
FIG. 8 is a cross-sectional view of a portion of an alternative embodiment system for providing medical electrical stimulation to a patient in accordance with principles of the present invention.

An alternative embodiment system 200 in accordance with principles of the present invention is shown in FIG. 8. The system 200 is similar to the system 20 (FIG. 1) previously described, and includes a lead assembly 202, the cannula 24, and a stylet 204. The lead assembly 202 is similar to the lead assembly 22 (FIG. 2A) previously described and includes a lead body 206 and a needle tip 208. The lead body 206 is, in one embodiment, identical to the lead body 26 (FIG. 2A) or the lead body 102 (FIG. 2B) previously described, and forms a central passage 210. The needle tip 208 is similar in many respects to the needle tip 28 (FIG. 2A) previously described, and again is configured to be permanently connected to the lead body 206 and releasably connected to the cannula 24. However, with the embodiment of FIG. 8, the needle tip 208 forms a central bore 212 extending axially therethrough. Upon final assembly of the lead body 206/needle tip 208, the axial bore 212 is aligned with and fluidly connected to, the central passage 210. With this configuration, then, the stylet 204 can be axially delivered through the central passage 210 and the axial bore 212 to perform probing operations distal the needle tip 208. For example, the stylet 204 can be employed to probe and find the desired stimulation site (e.g., operative proximity of a nerve of interest). Once the stimulation site is located, the lead assembly 202/cannula 24 is slid distally over and along the stylet 204 and operated as described above (e.g., the cannula 24 is removed from the lead assembly 202 once the needle tip 208 is located at the stimulation site). This technique may minimize trauma to the patient by using a smaller diameter probing stylet until the stimulation site is located.

The present invention provides a marked improvement over previous designs. By employing a needle tip as the electrode of a stimulation lead, the system provides a well defined electrode surface area (as compared to a conventional PNE lead), that can still be percutaneously introduced using a relatively thin tube or cannula. Further, once a nerve or other bodily tissue of interest has been located and the needle tip/electrode positioned in operative proximity thereto, the clinician is not required to move the needle tip/electrode to complete the temporary implantation procedure.

Although the present invention has been described with reference to preferred embodiments, workers skilled in the art will recognize that changes can be made in form and detail without departing from the spirit and scope of the present invention.

What is claimed is:

1. A system for providing a medical electrical stimulation to bodily tissue of a patient, the system comprising:
    a lead assembly including:
        a lead body having a distal section and a proximal section,
        a needle tip formed of an electrically conductive material and defining a proximal segment, an intermediate segment, and a distal segment tapering in outer diameter from the intermediate segment, wherein the proximal segment of the needle tip includes a post having a first diameter, and further wherein the intermediate segment extends distally from the post at a second diameter greater than the first diameter to form an abutment surface as a radial face of the intermediate segment,
        wherein the distal section of the lead body is connected to the proximal segment of the needle tip to establish an electrically conductive connection; and
    a cannula having a distal end, a proximal end, and a lumen;
        wherein the lead body is slidably disposed within the lumen and the distal end of the cannula is releasably connected to the needle tip adjacent the abutment surface such that upon final assembly the distal segment of the needle tip extends distal the distal end of the cannula to define a needle probe, and the distal end of the cannula selectively bears against the abutment surface.

2. The system of claim 1, wherein an outer diameter of the cannula and a maximum outer diameter of the needle tip are substantially equal.

3. The system of claim 2, wherein the outer diameter of the cannula and the maximum outer diameter of the needle tip are less than 0.05 inch.

4. The system of claim 1, wherein the needle tip and the cannula are sized to be percutaneously directed through a sacral foramen.

5. The system of claim 1, wherein the lead assembly is configured to conduct electrical energy from the proximal section of the lead body to the needle tip.

6. The system of claim 1, wherein the lead body has an outer diameter of not more than 0.03 inch.

7. The system of claim 1, wherein the system is configured such that the needle tip is disengagable from the cannula via an axial force applied to the proximal segment in a distal direction relative to the cannula.

8. The system of claim 1, wherein the lead body includes a wire wound as a coil.

9. The system of claim 8, wherein the wound coil defines a central passage, and further wherein the post is sized to be frictionally received within the central passage.

10. The system of claim 8, wherein the lead body further includes an electrically-non-conductive material covering portions of the wire such that at least one region of the wire along the distal segment is not covered by the wire to define an exposed electrode surface.

11. The system of claim 10, wherein the needle tip and the exposed electrode surface are operable to form a bipolar electrical assembly.

12. The system of claim 11, wherein the lead body includes first and second coaxially wound wire coils, the first coil being electrically connected to the needle tip and the second coil providing the exposed electrode surface.

13. The system of claim 1, wherein the distal end of the cannula is configured to releasably engage the post.

14. The system of claim 13, wherein engagement between the cannula and the post is one of an interference fit and a friction fit.

15. The system of claim 13, wherein the cannula forms a slot extending proximally from the distal end.

16. The system of claim 15, wherein the post includes a radial face sized to be slidably received within the slot.

17. The system of claim 1, wherein the lead body defines a central passage, the system further comprising:
a stylet slidably disposed within the central passage.

18. The system of claim 17, wherein the needle tip defines an axial bore extending from the proximal segment to the distal segment, the axial bore being fluidly connected to the central passage upon final assembly and sized to slidably receive the stylet.

19. The system of claim 1, wherein the distal section of the lead body has an outer diameter that is less than an outer diameter of the intermediate segment of the needle tip.

20. The system of claim 1, wherein a diameter of the lumen of the cannula is less than an outer diameter of the intermediate segment of the needle tip.

21. The system of claim 20, wherein an abutting interface between the abutment surface of the needle tip and the distal end of the cannula prevents retraction of the tip into the lumen.

22. A system for temporarily implanting a sacral peripheral nerve stimulator at a sacral location appropriate for electrically stimulating a sacral nerve, the system comprising:
a lead assembly including:
a lead body having a distal section and a proximal section,
a needle tip formed of an electrically conductive material and defining a proximal segment, an intermediate segment, and a distal segment tapering in outer diameter from the intermediate segment, wherein the proximal segment of the needle tip includes a post having a first diameter, and further wherein the intermediate segment extends distally from the post at a second diameter greater than the first diameter to form an abutment surface as a radial face of the intermediate segment,
wherein the distal section of the lead body is connected to the proximal segment of the needle tip to establish an electrically conductive connection; and
a cannula having a distal end, a proximal end, and a lumen;
wherein the lead body is slidably disposed within the lumen and the distal end of the cannula is releasably connected to the needle tip adjacent the abutment surface such that upon final assembly the distal segment of the needle tip extends distal the distal end of the cannula to define a needle probe, and the distal end of the cannula selectively bears against the abutment surface;
and further wherein the lead assembly and the cannula are, in combination, capable of being inserted through a foramen of the sacrum to position the needle tip in operative proximity with a sacral peripheral nerve to provide electrical stimulation to the sacral nerve.

23. The system of claim 22, wherein an outer diameter of the cannula and a maximum outer diameter of the needle tip are substantially equal.

\* \* \* \* \*